United States Patent
Moteki et al.

(10) Patent No.: US 9,158,013 B2
(45) Date of Patent: Oct. 13, 2015

(54) POSITRON EMISSION COMPUTED TOMOGRAPHY APPARATUS

(75) Inventors: Jun Moteki, Otawara (JP); Kenta Moriyasu, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 592 days.

(21) Appl. No.: 13/416,305

(22) Filed: Mar. 9, 2012

(65) Prior Publication Data

US 2012/0228511 A1 Sep. 13, 2012

(30) Foreign Application Priority Data

Mar. 9, 2011 (JP) ................... 2011-052020

(51) Int. Cl.
| | |
|---|---|
| G06T 11/00 | (2006.01) |
| G06K 9/36 | (2006.01) |
| G01T 1/164 | (2006.01) |
| G01T 1/29 | (2006.01) |
| A61B 6/03 | (2006.01) |
| A61B 6/00 | (2006.01) |

(52) U.S. Cl.
CPC .............. *G01T 1/2985* (2013.01); *A61B 6/037* (2013.01); *A61B 6/46* (2013.01); *G01T 1/1647* (2013.01); *G06K 9/36* (2013.01); *G06T 11/003* (2013.01)

(58) Field of Classification Search
CPC ..... G01T 1/2992; G01T 1/164; G06T 11/003; G06K 9/36; G06K 9/464–9/4647
USPC .................................................. 250/363.03
See application file for complete search history.

(56) References Cited

U.S. PATENT DOCUMENTS

| 7,554,915 B2* | 6/2009 | Bauer et al. ................... 370/235 |
| 2004/0173750 A1* | 9/2004 | Welsh et al. ............... 250/336.1 |
| 2004/0222379 A1* | 11/2004 | Cook ........................ 250/363.03 |
| 2007/0278409 A1* | 12/2007 | Cook et al. ............... 250/363.03 |

FOREIGN PATENT DOCUMENTS

| JP | 01-221143 A | 9/1989 |
| JP | 06-342075 A | 12/1994 |
| JP | 2005-207995 A | 8/2005 |
| JP | 2005-305165 A | 11/2005 |
| JP | 2007-537458 A | 12/2007 |
| JP | 2008-190901 | 8/2008 |

(Continued)

OTHER PUBLICATIONS

Japan Industries Association of Radiological Systems "Medical Image/Radiological Equipment Hand Book" published by Nago Bijutsu Insatsu Kabushiki Kaisha, with Partial English Translation, 2001, 3 pages.

(Continued)

*Primary Examiner* — Casey Bryant
(74) *Attorney, Agent, or Firm* — Oblon, McClelland, Maier & Neustadt, L.L.P.

(57) ABSTRACT

A positron emission computed tomography apparatus according to an embodiment includes a detector, a buffer, and a regulating unit. The detector detects annihilation radiation. The buffer stores therein event data generated based on an output signal from the detector. The regulating unit regulates the amount of the event data read from the buffer during a high count rate period of the events at which the annihilation radiation is detected.

15 Claims, 15 Drawing Sheets

(56) References Cited

FOREIGN PATENT DOCUMENTS

| | | |
|---|---|---|
| JP | 2010-035714 A | 2/2010 |
| JP | 2010-185675 A | 8/2010 |
| JP | 2010-261830 A | 11/2010 |

OTHER PUBLICATIONS

Office Action issued Sep. 24, 2014 in Japanese Patent Application No. 2011-052020 (with English language translation).

Office Action issued Mar. 3, 2015 in Japanese Patent Application No. 2011-052020.

* cited by examiner

POSITRON EMISSION COMPUTED TOMOGRAPHY APPARATUS

CROSS-REFERENCE TO RELATED APPLICATIONS

This application is based upon and claims the benefit of priority from Japanese Patent Application No. 2011-052020, filed on Mar. 9, 2011; the entire contents of which are incorporated herein by reference.

FIELD

Embodiments described herein relate generally to a positron emission computed tomography apparatus.

BACKGROUND

As a nuclear medicine imaging apparatus, Positron Emission computed Tomography (PET) apparatuses are conventionally known. To perform an image taking process using a PET apparatus, an examined subject is dosed with a compound or a radiopharmaceutical labeled with a positron emitting nuclide. The compound or the radiopharmaceutical with which the examined subject was dosed travels within the examined subject's body, and the positron emitting nuclide is taken into a body tissue of the examined subject. The positron emitting nuclide releases positrons, so that the released positrons are coupled with electrons and annihilated. At this time, the positrons release a pair of annihilation radiation rays (which may also be referred to as "gamma rays" or "annihilation gamma rays") in substantially opposite directions. The PET apparatus detects the annihilation radiation rays by using a detector arranged in a ring formation so as to surround the examined subject and generates coincidence counting information (hereinafter, a "coincidence list") from the detection result. Further, the PET apparatus performs a reconstructing process through a back-projection process by using the generated coincidence list and generates a PET image.

Incidentally, during the process of generating the coincidence list from the detection result, the PET apparatus generates data (hereinafter, "event data") based on an output signal from the detector and transfers the generated event data to a subsequent processing stage. Because this transfer process and the processing at the subsequent stage are subject to hardware restrictions, the PET apparatus usually includes a buffer for storing the event data therein so as to regulate the amount of the event data to be transferred. However, during a high count rate period in which a large number of annihilation radiation rays are detected in a unit time period, the PET apparatus may not be able to regulate the amount of the event data appropriately.

DETAILED DESCRIPTION

A positron emission computed tomography apparatus according to an embodiment includes a detector, a buffer, and a regulating unit. The detector is configured to detect annihilation radiation. The buffer is configured to store therein event data generated based on an output signal from the detector. The regulating unit is configured to regulate an amount of event data read from the buffer, during a high count rate period of events at which the annihilation radiation is detected.

In the following sections, exemplary embodiments of a positron emission computed tomography apparatus will be explained, with reference to the accompanying drawings.

Figure 1:
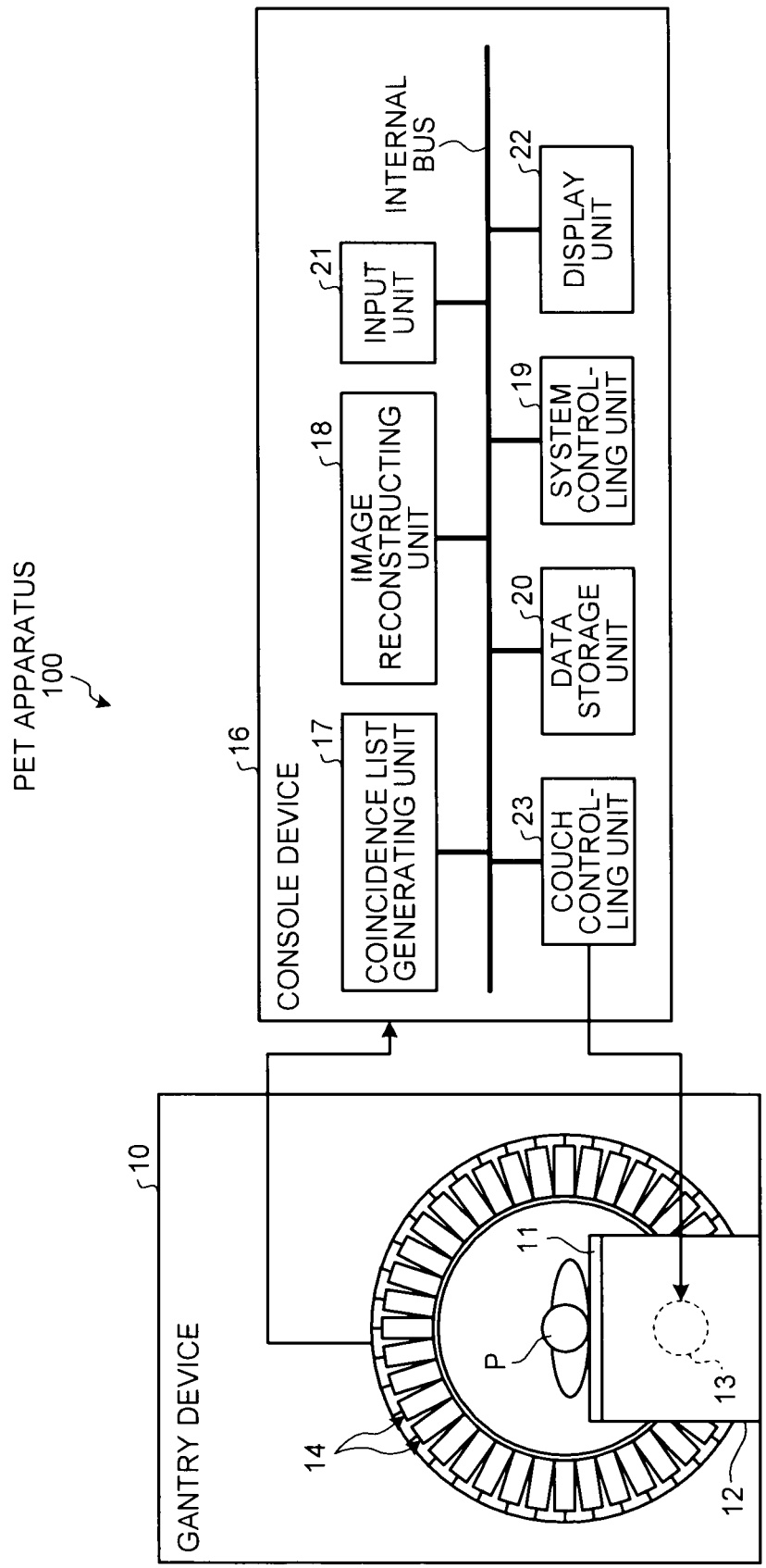
FIG. 1 is a block diagram of a PET apparatus according to a first embodiment.

To start with a first embodiment, FIG. 1 is a block diagram of a PET apparatus 100 according to the first embodiment. As shown in FIG. 1, the PET apparatus 100 according to the first embodiment includes a gantry device 10 and a console device 16.

As shown in FIG. 1, the gantry device 10 includes a couchtop 11, a couch 12, a couch driving unit 13, and detector modules 14. Also, the gantry device 10 has a hollow serving as an image-taking opening. The couchtop 11 is a bed on which an examined subject P lies down and is positioned on top of the couch 12. Under the control of a couch controlling unit 23 (explained later), the couch driving unit 13 moves the couchtop 11. For example, by moving the couchtop 11, the couch driving unit 13 moves the examined subject P into the space inside the image-taking opening of the gantry device 10.

The detector modules 14 detect annihilation radiation rays emitted from the examined subject P. As shown in FIG. 1, within the gantry device 10, the plurality of detector modules 14 are arranged in a ring formation so as to surround the examined subject P.

Figure 2:
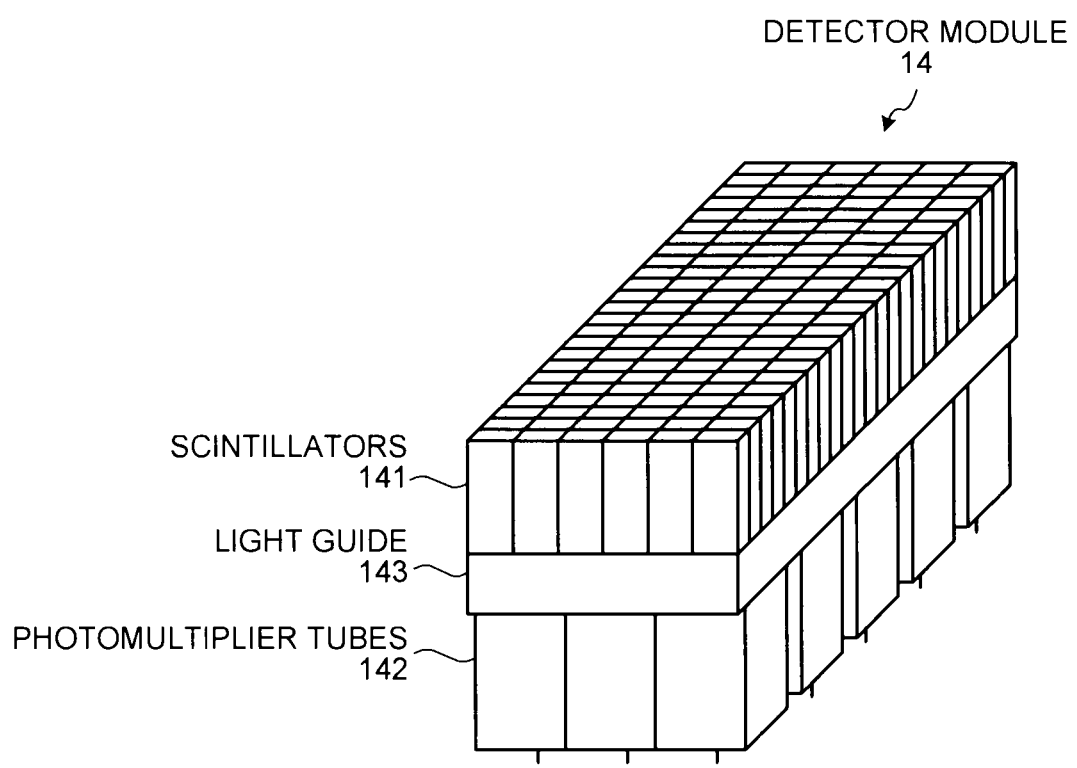
FIG. 2 is a drawing for explaining detector modules according to the first embodiment.

FIG. 2 is a drawing for explaining the detector modules 14 according to the first embodiment. Each of the detector modules 14 is an Anger-type detector that uses a photon counting method. As shown in FIG. 2, each of the detector modules 14 includes scintillators 141, photomultiplier tubes (PMTs) 142, and a light guide 143.

The scintillators 141 convert the annihilation radiation rays that are emitted from the examined subject P and entered therein into visible light (hereinafter, "scintillation light") and output the scintillation light resulting from the conversion.

The scintillators 141 are configured with scintillator crystals of, for example, NaI (sodium iodide), BGO (bismuth germanate), LYSO (lutetium yttrium oxyorthosilicate), LSO (lutetium oxyorthosilicate), LGSO (lutetium gadolinium oxyorthosilicate), or the like. As shown in FIG. 2, the scintillators 141 are arranged in a two-dimensional formation. The photomultiplier tubes 142 multiply the scintillation light output from the scintillators 141 and covert the multiplied scintillation light into an electric signal. As shown in FIG. 2, the plurality of photomultiplier tubes 142 are provided. The light guide 143 transfers the scintillation light output from the scintillator 141 to the photomultiplier tubes 142. The light guide 143 is configured by using, for example, a plastic material having an excellent light transmitting characteristic.

Each of the photomultiplier tubes 142 includes a photocathode that receives the scintillation light and generates photoelectrons; multiple stages of dynodes that create electric fields for accelerating the generated photoelectrons; and an anode from which electrons flow out. The electrons emitted from the photocathode due to the photoelectric effect are accelerated toward a dynode and collide with the surface of the dynode, so as to knock out additional electrons. When this phenomenon is repeated at the multiple stages of dynodes, the number of electrons is multiplied in the manner of an avalanche so that the number of electrons reaches as many as approximately 1 million at the anode. In this example, the gain factor of the photomultiplier tube 142 is 1 million times. To cause this multiplication utilizing the avalanche phenomenon, a voltage of 1000 volts or higher is usually applied to between the dynodes and the anode.

In this manner, the detector modules 14 detect the annihilation radiation rays emitted from the examined subject P, by converting the annihilation radiation rays emitted from the examined subject P into the scintillation light by using the scintillators 141 and further converting the converted scintillation light into the electric signal (hereinafter, "detector signal") by using the photomultiplier tubes 142.

In the first embodiment, the plurality of detector modules 14 are divided into a plurality of blocks, and an event data acquiring unit 15 is provided for each of the blocks. For example, in the first embodiment, one detector module 14 forms one block. Thus, each of the detector modules 14 includes one event data acquiring unit 15. The correspondence relationship between each block and the quantity of detector modules 14 is arbitrary. The event data acquiring units 15 will be explained later in detail.

Returning to the description of FIG. 1, the console device 16 includes a coincidence list generating unit 17, an image reconstructing unit 18, a system controlling unit 19, a data storage unit 20, an input unit 21, a display unit 22, and the couch controlling unit 23. The functional units included in the console device 16 are connected to one another via an internal bus.

The input unit 21 is configured with a mouse and/or a keyboard used by an operator of the PET apparatus 100 for inputting various types of instructions and various types of settings and is configured so as to transfer the input various types of instructions and settings to the system controlling unit 19. The display unit 22 is a monitor or the like referenced by the operator. Under the control of the system controlling unit 19, the display unit 22 displays PET images and a Graphical User Interface (GUI) for receiving the various types of instructions and the various types of settings from the operator. The couch controlling unit 23 controls the couch driving unit 13.

The data storage unit 20 stores therein various types of data used in the PET apparatus 100. For example, the data storage unit 20 stores therein the event data transferred from the gantry device 10, the coincidence list generated by the coincidence list generating unit 17, and PET images reconstructed by the image reconstructing unit 18. The data storage unit 20 is realized with, for example, a semiconductor memory element such as a Random Access Memory (RAM) or a flash memory, a hard disk, or an optical disk.

The coincidence list generating unit 17 generates the coincidence list by using the event data acquired by the event data acquiring unit 15. More specifically, the coincidence list generating unit 17 reads the event data stored in the data storage unit 20 and searches for a pair of pieces of event data representing a pair of annihilation radiation rays emitted from a positron that are coincident and counted at the same time. Further, the coincidence list generating unit 17 generates the pair of pieces of event data found in the search into the coincidence list and stores the generated coincidence list into the data storage unit 20.

The image reconstructing unit 18 reconstructs the PET image. More specifically, the image reconstructing unit 18 reconstructs the PET image by reading the coincidence list stored in the data storage unit 20 as projection data and performing a back-projection process on the read projection data. Further, the image reconstructing unit 18 stores the reconstructed PET image into the data storage unit 20.

The system controlling unit 19 executes overall control of the PET apparatus 100 by controlling the gantry device 10 and the console device 16. For example, the system controlling unit 19 controls image taking processes performed by the PET apparatus 100.

The functional units described above such as the coincidence list generating unit 17, the image reconstructing unit 18, and the system controlling unit 19 are configured by using an integrated circuit such as an Application Specific Integrated Circuit (ASIC) or a Field Programmable Gate Array (FPGA) or an electronic circuit such as a Central Processing Unit (CPU) or a Micro Processing Unit (MPU).

Figure 3:
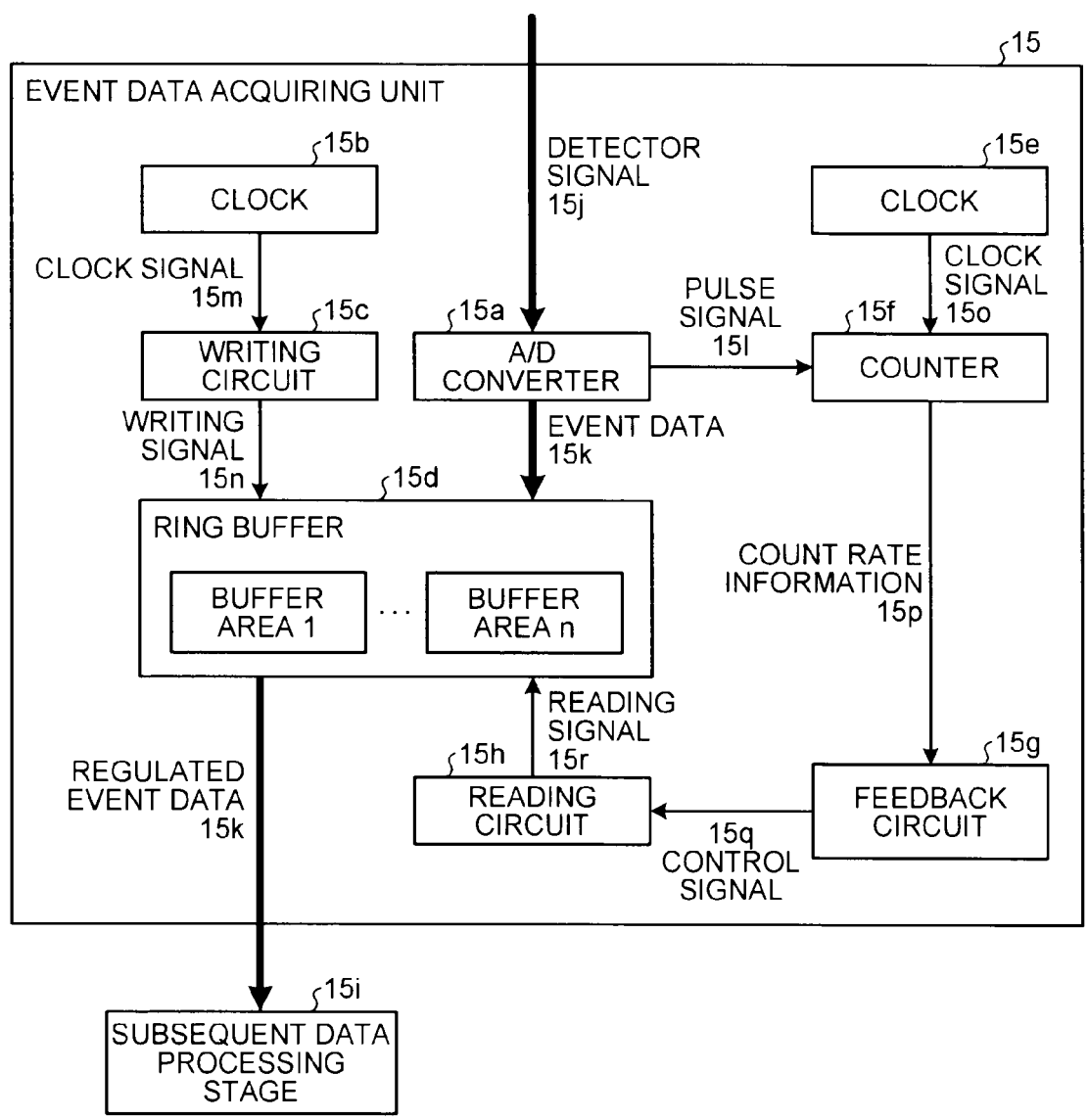
FIG. 3 is a block diagram of an event data acquiring unit according to the first embodiment.

Next, the event data acquiring unit 15 according to the first embodiment will be explained in details. FIG. 3 is a block diagram of the event data acquiring unit 15 according to the first embodiment. As shown in FIG. 3, the event data acquiring unit 15 includes an analog/digital (A/D) converter 15a, a clock 15b, a writing circuit 15c, a ring buffer 15d, another clock 15e, a counter 15f, a feedback circuit 15g, and a reading circuit 15h.

In this situation, as shown in FIG. 3, the ring buffer 15d according to the first embodiment is a ring buffer including buffer areas of which the total quantity is n. Further, as shown in FIG. 3, the counter 15f generates count rate information 15p. The count rate information 15p indicates a count rate of detector signals 15j (i.e., the quantity of the detector signals 15j counted in a unit time period). Further, the feedback circuit 15g and the reading circuit 15h judge whether it is currently a high count rate period based on the count rate information. When it is determined that it is currently a high count rate period, event data 15k are read from a part of the n buffer areas included in the ring buffer 15d. For example, during a high count rate period, the reading circuit 15h reads only the event data 15k stored in buffer areas 1 to i. In the following sections, operations performed by the functional units will be explained.

The A/D converter 15a receives inputs of the detector signals 15j and outputs the event data 15k and pulse signals 15l. More specifically, when having received an input of a detector signal 15j, which is analog data, the A/D converter 15a generates event data 15k by converting the analog data into digital data and outputs the generated event data 15k to the ring buffer 15d. The event data 15k includes, for example, detection positions of the annihilation radiation rays (e.g., identification information of the scintillators 141), energy values (e.g., strengths of the detector signals 15j), and detection times (e.g., absolute times or elapsed time periods since the start of the image taking process).

Further, when having received an input of a detector signal 15j, the A/D converter 15a generates one pulse signal 15l and outputs the generated pulse signal 15l to the counter 15f. Accordingly, the A/D converter 15a receives inputs of a plurality of detector signals 15j over the course of time. Every time the A/D converter 15a receives an input, the A/D converter 15a generates one pulse signal 15l.

The clock 15b generates a clock signal 15m and outputs the generated clock signal 15m to the writing circuit 15c. The writing circuit 15c receives inputs of the clock signals 15m and outputs writing signals 15n to the ring buffer 15d in synchronization with the clock signals 15m. Further, the writing circuit 15c outputs the writing signals 15n so that the pieces of event data 15k are sequentially written into the buffer areas included in the ring buffer. For example, the writing circuit 15c outputs the writing signals 15n indicating "write to the buffer area 1", "write to the buffer area 2" and so on at intervals of 10 nanoseconds.

The ring buffer 15d is the ring buffer including the buffer areas of which the total quantity is n. The ring buffer 15d receives inputs of the pieces of event data 15k and the writing signals 15n and sequentially stores the pieces of event data 15k into the buffer areas according to the writing signals 15n. For example, the ring buffer 15d sequentially stores the pieces of event data 15k into the buffer areas, for example, into the buffer area 1, the buffer area 2, and so on at intervals of 10 nanoseconds. When the pieces of event data 15k have been stored into the buffer areas up to the buffer area n, the ring buffer 15d stores more pieces of event data 15k, starting with the buffer area 1 again.

The clock 15e generates a clock signal 15o and outputs the generated clock signal 15o to the counter 15f. The counter 15f receives inputs of the clock signals 15o and the pulse signals 15l, counts the quantity of the pulse signals 15l that are input in a unit time period, and generates the count rate information 15p. Further, the counter 15f outputs the generated count rate information 15p to the feedback circuit 15g.

Figure 4:
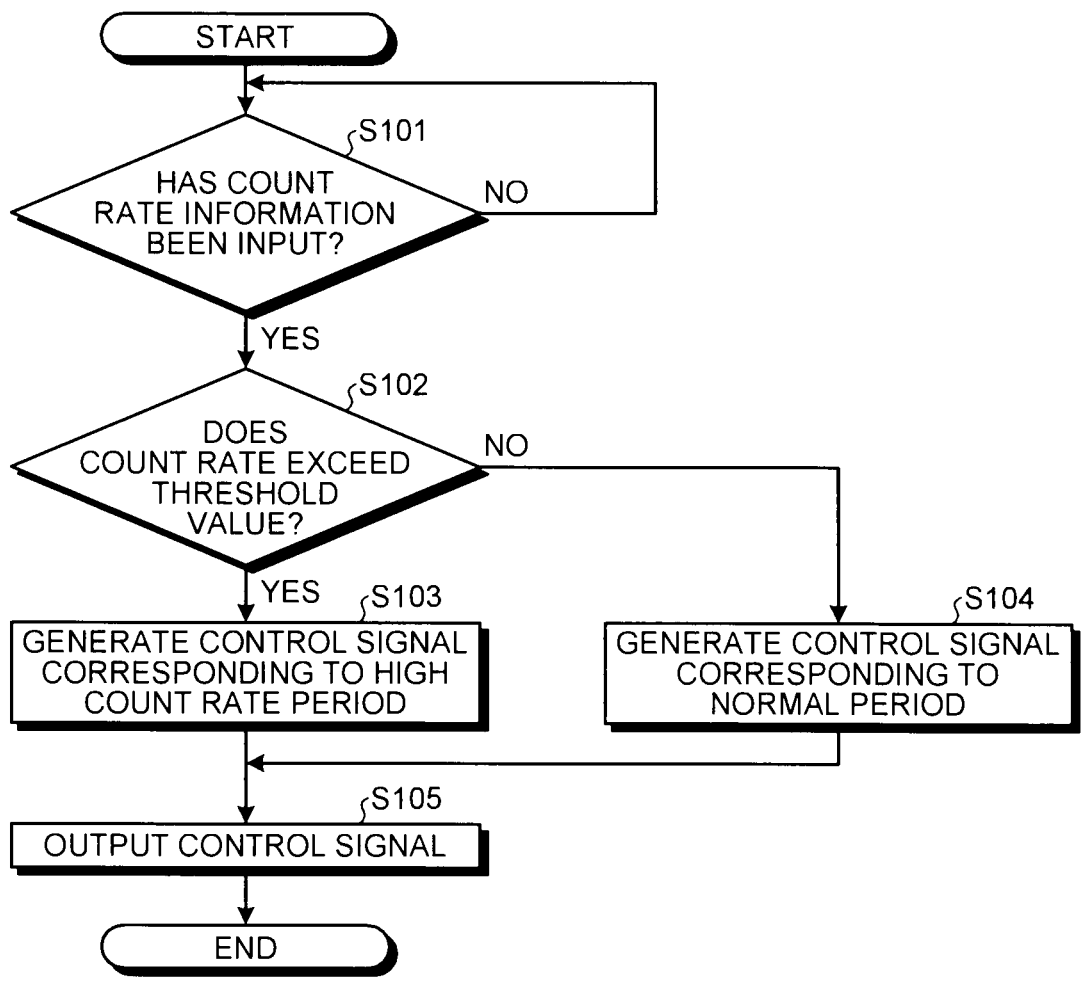
FIG. 4 is a flowchart of a processing procedure performed by a feedback circuit according to the first embodiment.

The feedback circuit 15g receives an input of the count rate information 15p, generates a control signal 15q based on the count rate information 15p, and outputs the generated control signal 15q to the reading circuit 15h. FIG. 4 is a flowchart of a processing procedure performed by the feedback circuit 15g according to the first embodiment.

As shown in FIG. 4, when having received an input of the count rate information 15p (step S101: Yes), the feedback circuit 15g judges whether the count rate indicated by the count rate information 15p exceeds a threshold value (step S102). When the count rate exceeds the threshold value (step S102: Yes), the feedback circuit 15g generates a control signal 15q indicating that it is currently a high count rate period (step S103). On the contrary, when the count rate does not exceed the threshold value (step S102: No), the feedback circuit 15g generates a control signal 15q indicating that it is currently a normal period (step S104). Further, the feedback circuit 15g outputs the control signal 15q generated at step S103 or step S104 to the reading circuit 15h (step S105).

Figure 5:
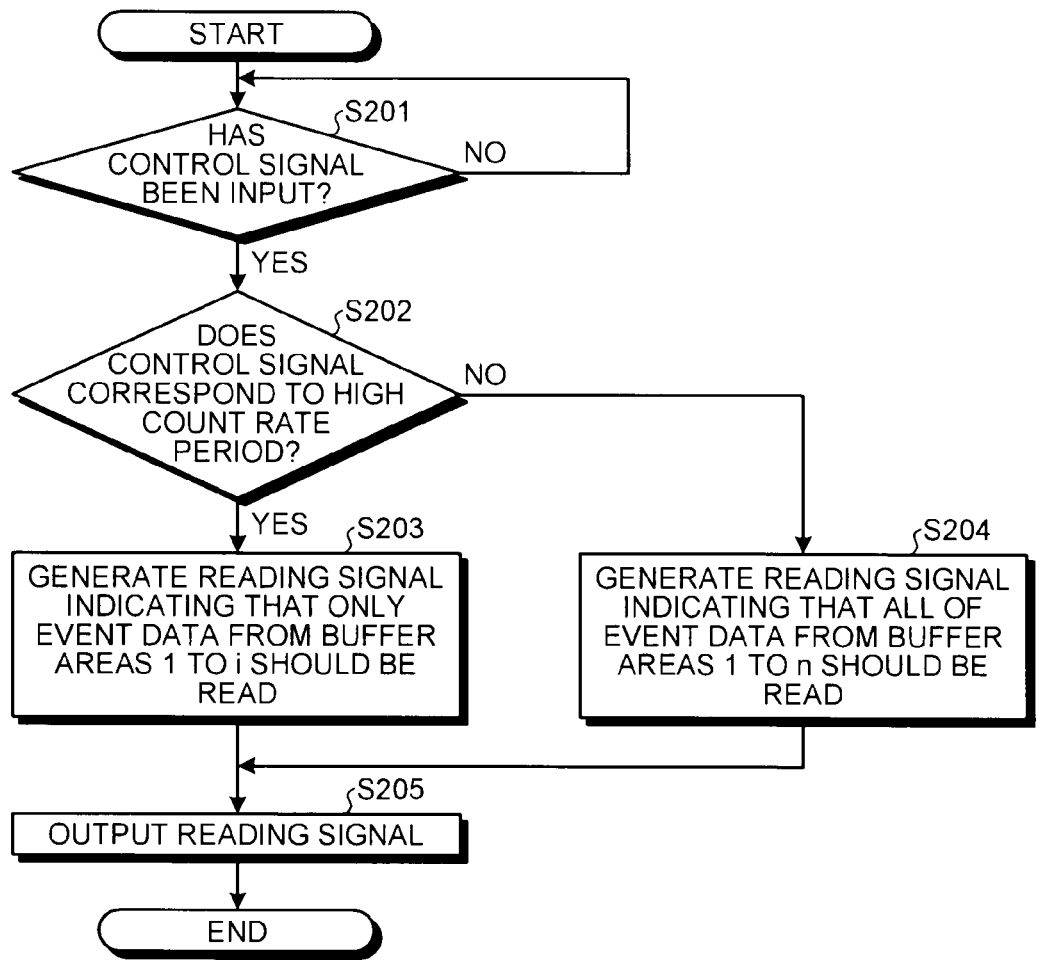
FIG. 5 is a flowchart of a processing procedure performed by a reading circuit according to the first embodiment.

The reading circuit 15h receives an input of the control signal 15q, generates a reading signal 15r based on the control signal 15q, and outputs the generated reading signal 15r to the ring buffer 15d. FIG. 5 is a flowchart of a processing procedure performed by the reading circuit 15h according to the first embodiment.

As shown in FIG. 5, when having received an input of the control signal 15q (step S201: Yes), the reading circuit 15h judges whether the control signal 15q is one indicating that it is currently a high count rate period (step S202). When the control signal 15q is one indicating that it is currently a high count rate period (step S202: Yes), the reading circuit 15h generates a reading signal 15r indicating that only the pieces of event data 15k stored in the buffer areas 1 to i should be read (step S203). On the contrary, when the control signal 15q is one indicating that it is currently a normal period (step S202: No), the reading circuit 15h generates a reading signal 15r indicating that the pieces of event data 15k stored in all of the buffer areas 1 to n should be read (step S204). Further, the reading circuit 15h outputs the reading signal 15r generated at step S203 or step S204 to the ring buffer 15d (step S205).

The ring buffer 15d receives an input of the reading signal 15r and outputs the event data 15k to a subsequent data processing stage 15i according to the reading signal 15r. The event data 15k in this situation is event data 15k of which the amount that is read is regulated according to the reading signal 15r. In other words, during the high count rate period, the ring buffer 15d outputs only the pieces of event data 15k stored in the buffer areas 1 to i, according to the reading signal 15r. On the contrary, during the normal period, the ring buffer 15d outputs the pieces of event data 15k stored in all of the buffer areas 1 to n, according to the reading signal 15r. As explained here, the event data 15k output from the ring buffer 15d is the event data 15k of which the amount that is read is regulated according to the reading signal 15r. The timing with which the ring buffer 15d outputs the event data 15k corresponds to, for example, the time at which the event data 15k has been stored into all of the n buffer areas, while the high count rate is at a maximum value that can be expected.

As explained above, the PET apparatus 100 according to the first embodiment regulates, during the high count rate period, the amount of the event data read from the ring buffer. More specifically, the PET apparatus 100 judges whether it is currently a high count rate period based on the count rate information and, when the PET apparatus 100 has determined that it is currently a high count rate period, the PET apparatus 100 reads the event data from a part of the plurality of buffer areas included in the ring buffer. With this arrangement, according to the first embodiment, it is possible to appropriately regulate the amount of the event data even during a high count rate period.

In the first embodiment, the method was explained by which only the pieces of event data 15k stored in the buffer areas 1 to i are read; however, the exemplary embodiments are not limited to this example. For instance, another method is acceptable by which pieces of event data 15k are read from such buffer areas of which the quantity is i and that are selected out of the n buffer areas in an inconsecutive manner, e.g., from the buffer areas 1, 3, and 5. In this manner, the pieces of event data 15k that are not read are dispersed appropriately.

Further, in the first embodiment, the method was explained by which, during a high count rate period, the pieces of event data 15k are read from the buffer areas of which the quantity is fixed to i; however, the exemplary embodiments are not limited to this example. For instance, another method is acceptable by which the quantity of the buffer areas from which pieces of event data 15k are read is varied according to the count rate. With this arrangement where the quantity of the buffer areas is varied, it is possible to appropriately regulate the amount of the event data according to the count rate at the time.

Next, a second embodiment will be explained. While using the method according to the first embodiment as a base, the PET apparatus 100 according to the second embodiment executes control so that the regulations on the amounts of the event data for the different blocks are synchronized among all the blocks.

Figure 6:
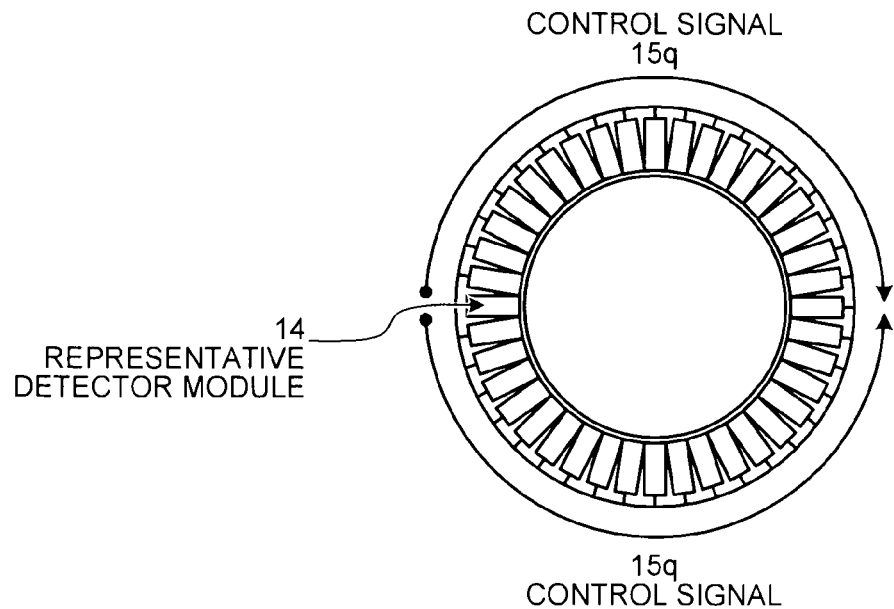
FIG. 6 is a drawing for explaining synchronization among blocks according to a second embodiment.
Figure 7:
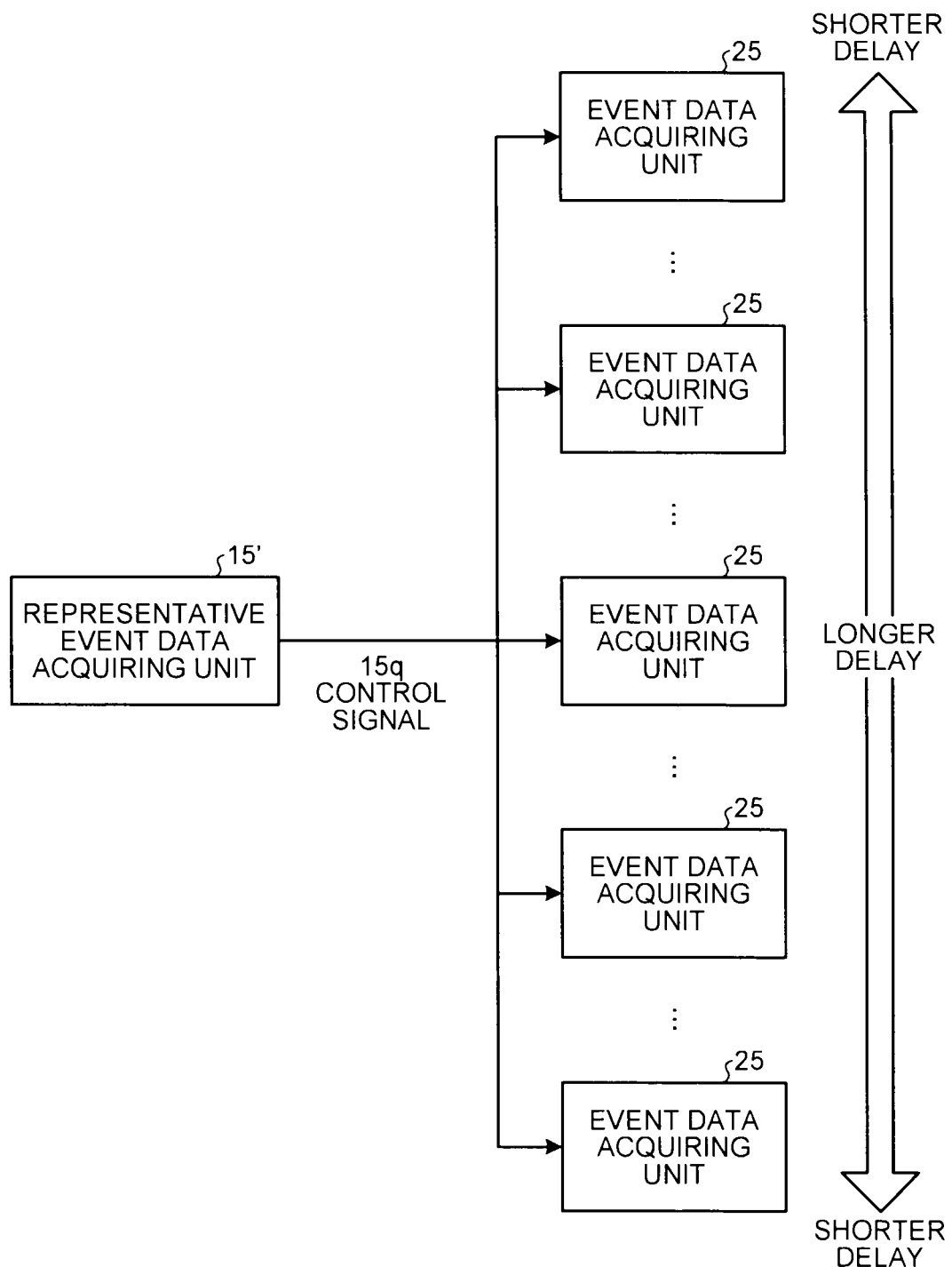
FIG. 7 is another drawing for explaining the synchronization among the blocks according to the second embodiment.

In the second embodiment, the plurality of detector modules 14 are divided into a plurality of blocks. For example, one detector module 14 forms one block. FIGS. 6 and 7 are drawings for explaining the synchronization among the blocks according to the second embodiment. As shown in FIG. 6, according to the second embodiment, of the detector modules 14 arranged in the ring formation so as to surround the examined subject P, a detector module 14 positioned on the left side, for example, is designated as a representative detector module 14. The representative detector module 14 includes a representative event data acquiring unit 15'. Each of the other detector modules 14 includes an event data acquiring unit 25. Further, the representative event data acquiring unit 15' transmits a control signal 15q to the other event data acquiring units 25. The other event data acquiring units 25 regulate the amount of the event data read from the ring buffer according to the control signal 15q transmitted from the representative event data acquiring unit 15'.

In this situation, to realize the synchronization among the blocks, it is desirable to configure the control signal 15q so as to arrive at all the detector modules 14 at the same time. For this reason, as shown in FIG. 7, delay circuits having mutually-different delay periods according to distances from the representative event data acquiring unit 15' are inserted. In other words, a delay circuit having the longest delay period is inserted for the representative event data acquiring unit 15'. For the other event data acquiring units 25, the delay circuits are inserted in such a manner that the longer the distance from the representative event data acquiring unit 15' is, the shorter is the delay period. The delay periods may be set to values that are calculated in a calibration process performed in advance. Further, it is also possible to configure the ring buffer 15d included in the representative event data acquiring unit 15' so as to have a larger capacity than those of ring buffers 25d included in the other event data acquiring units 25.

Figure 8:
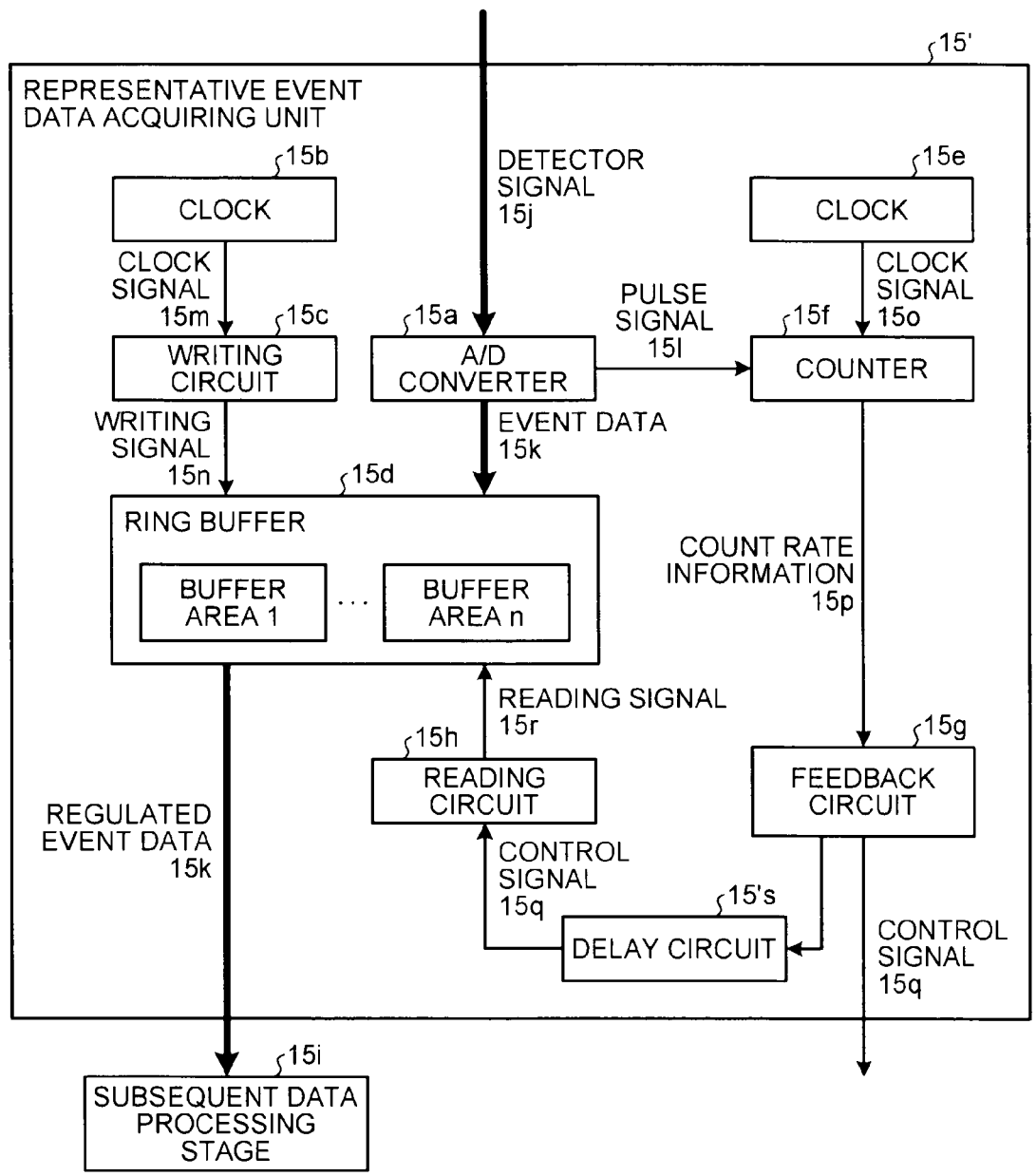
FIG. 8 is a block diagram of a representative event data acquiring unit according to the second embodiment.

FIG. 8 is a block diagram of the representative event data acquiring unit 15' according to the second embodiment. In FIG. 8, some of the functional units that operate in the same manner as those in the event data acquiring unit 15 explained with reference to FIG. 3 will be referred to by using the same reference characters as in FIG. 3.

As shown in FIG. 8, the representative event data acquiring unit 15' includes a delay circuit 15's disposed between the feedback circuit 15g and the reading circuit 15h. In other words, the feedback circuit 15g outputs the generated control signal 15q to the reading circuit 15h via the delay circuit 15's, instead of outputting the generated control signal 15q directly to the reading circuit 15h. Further, the feedback circuit 15g transfers the control signal 15q to the other event data acquiring units 25.

Figure 9:
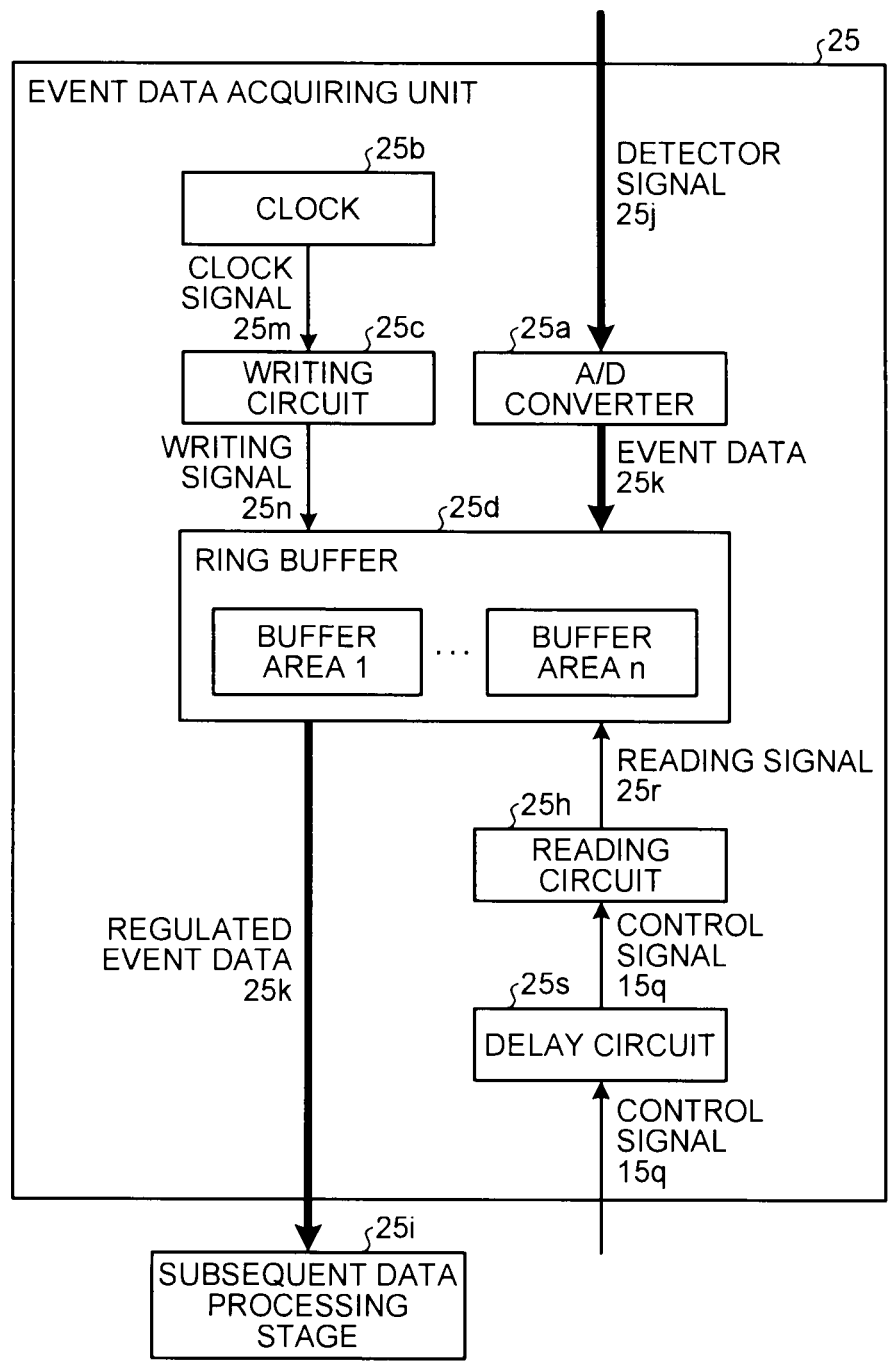
FIG. 9 is a block diagram of an event data acquiring unit according to the second embodiment.

FIG. 9 is a block diagram of the event data acquiring unit 25 according to the second embodiment. An A/D converter 25a operates in the same manner as the A/D converter 15a shown in FIG. 3. A clock 25b operates in the same manner as the clock 15b shown in FIG. 3. A writing circuit 25c operates in the same manner as the writing circuit 15c shown in FIG. 3. A ring buffer 25d operates in the same manner as the ring buffer 15d shown in FIG. 3. A reading circuit 25h operates in the same manner as the reading circuit 15h shown in FIG. 3. A subsequent data processing stage 25i operates in the same manner as the subsequent data processing stage 15i shown in FIG. 3.

As shown in FIG. 9, the event data acquiring unit 25 includes a delay circuit 25s disposed at a preceding stage of the reading circuit 25h. The control signal 15q transmitted from the representative event data acquiring unit 15' is output to the reading circuit 25h via the delay circuit 25s.

As explained above, the PET apparatus 100 according to the second embodiment executes control so that the regulations on the amounts of the event data for the different blocks are synchronized among all the blocks. Thus, it is possible to appropriately regulate the amount of the event data.

More specifically, the pieces of event data stored in one of the buffer areas of one of the detector module 14 are, for example, pieces of event data in a 10-nanosecond time period. Thus, when the amounts of the event data are regulated in synchronization with the other detector modules 14, the pieces of data stored in such buffer areas that are identified with mutually the same number are discarded for all the blocks. In other words, it is possible to discard the pieces of event data in a certain 10-nanosecond time period for all the blocks. As a result, it is possible to discard the pieces of event data together that can form a pair.

If pieces of event data were discarded randomly, discarding n pieces of event data would mean discarding n pairs of pieces of event data. As a result, it would be impossible to utilize the event data in a sufficiently effective manner in terms of image quality. Thus, there would be a possibility that an image having an artifact is output. In contrast, according to the second embodiment, because each of the discarded pieces of event data is discarded together with the piece of data in the pair, it is possible to utilize the event data in a sufficiently effective manner.

In the second embodiment, the method was explained by which the representative detector module 14 transmits the control signal 15q to the other detector modules 14; however, the exemplary embodiments are not limited to this example. For instance, another method is acceptable by which a representative feedback circuit is provided on the outside of the detector modules 14 so that the detector modules 14 transmit and receive the count rate information and the control signal to and from the representative feedback circuit.

Figure 10:
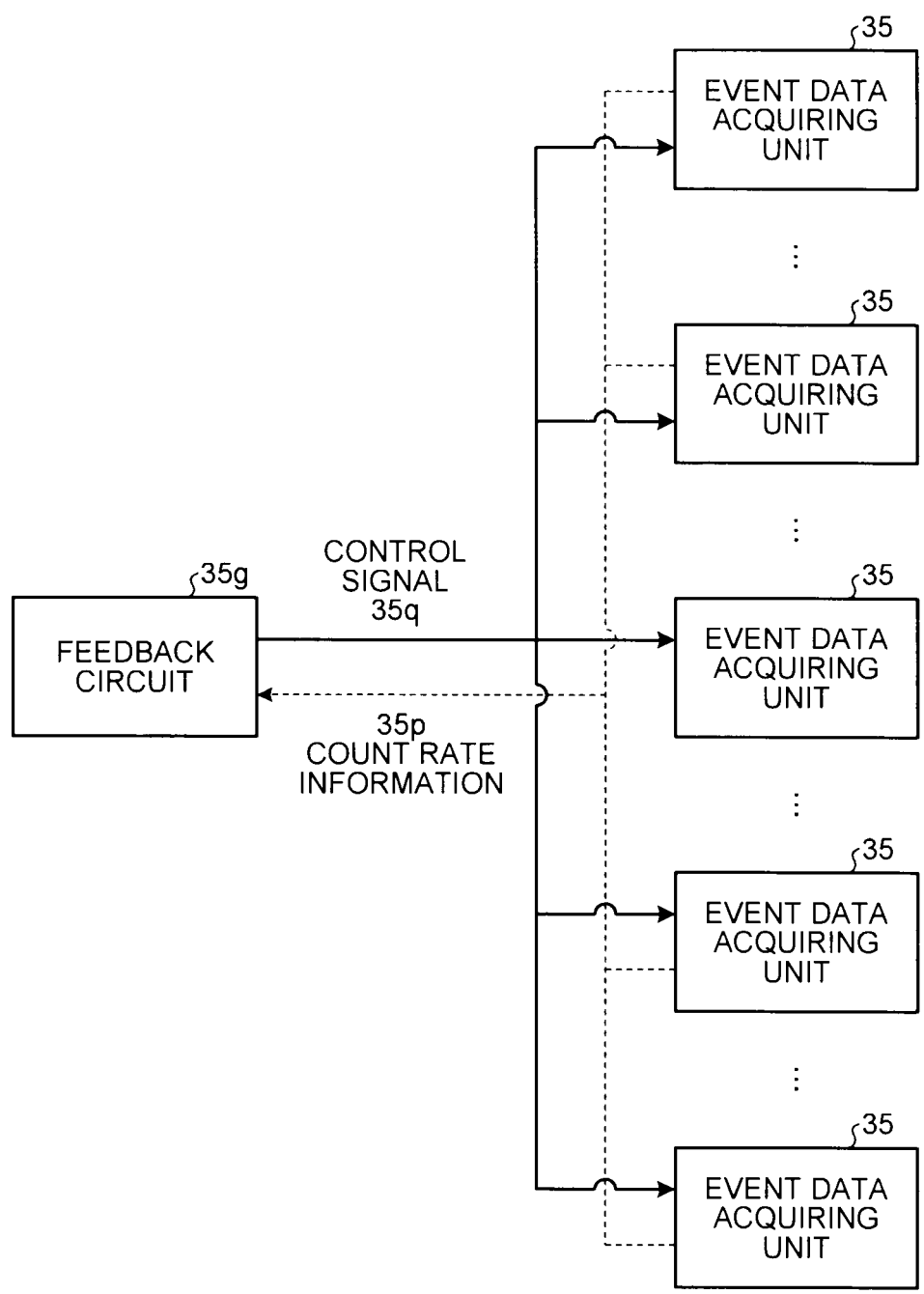
FIG. 10 is a drawing for explaining another method of synchronization among blocks according to the second embodiment.

FIG. 10 is a drawing for explaining said another method of synchronization among the blocks according to the second embodiment. As shown in FIG. 10, for example, a representative feedback circuit 35g is provided, so that each of an event data acquiring units 35 transmits count rate information 35p generated individually, to the representative feedback circuit 35g. The representative feedback circuit 35g judges whether it is currently a high count rate period, based on the count rate information 35p transmitted from each of the event data acquiring units 35 and generates a control signal 35q indicating that it is currently a high count rate period or a control signal 35q indicating that it is currently a normal period. Further, the representative feedback circuit 35g transmits the generated control signal 35q to each of the detector modules 14. As mentioned earlier, it is desirable to configure the control signal 35q so as to arrive at all the detector modules 14 at the same time. For this reason, delay circuits having mutually-different delay periods according to distances from the feedback circuit 35g are inserted.

Figure 11:
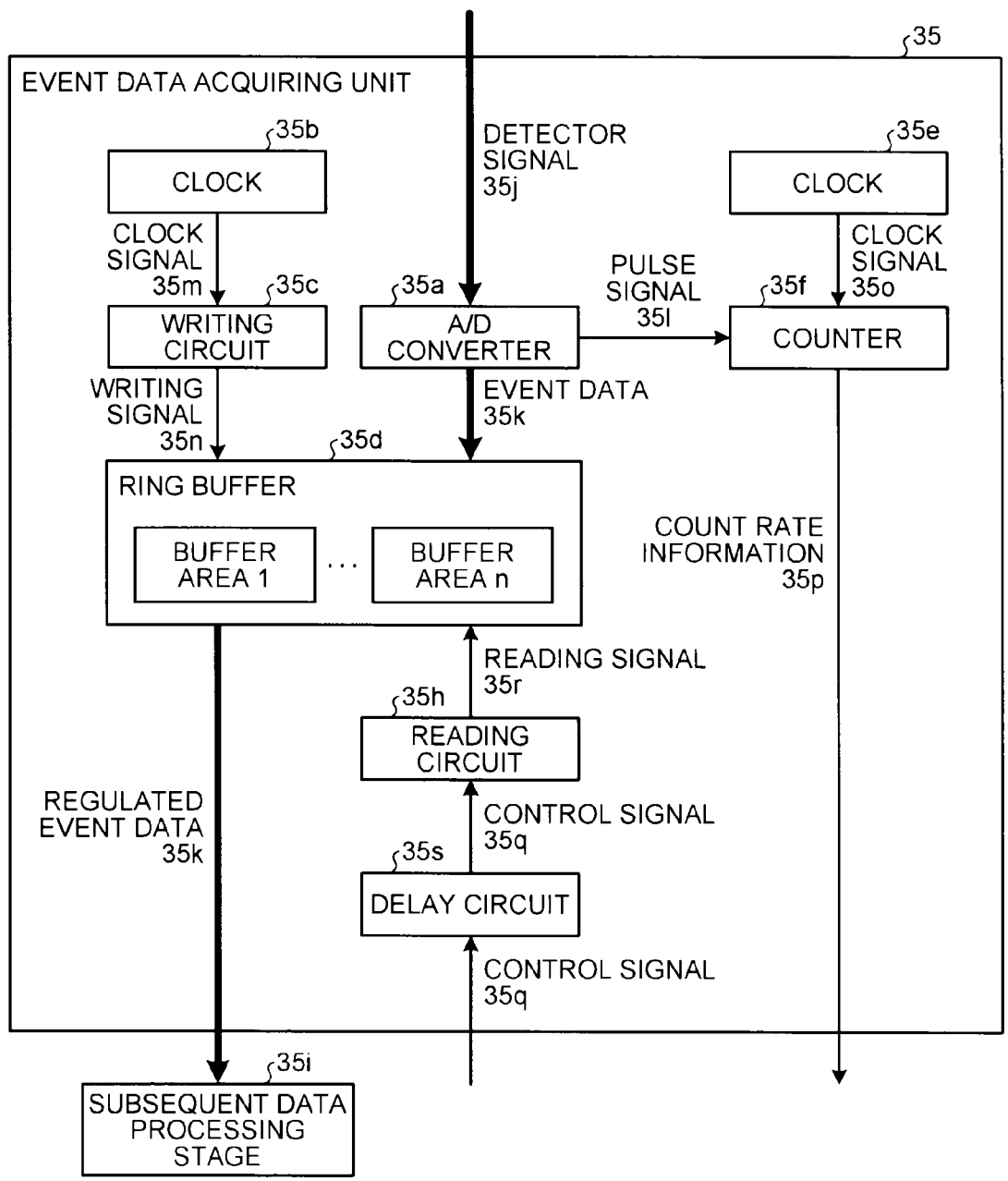
FIG. 11 is a block diagram of an event data acquiring unit using another method according to the second embodiment.

FIG. 11 is a block diagram of the event data acquiring unit 35 according to said another method of the second embodiment. An A/D converter 35a operates in the same manner as the A/D converter 15a shown in FIG. 3. A clock 35b operates in the same manner as the clock 15b shown in FIG. 3. A writing circuit 35c operates in the same manner as the writing circuit 15c shown in FIG. 3. A ring buffer 35d operates in the same manner as the ring buffer 15d shown in FIG. 3. A clock 35e operates in the same manner as the clock 15e shown in FIG. 3. A counter 35f operates in the same manner as the counter 15f shown in FIG. 3. A reading circuit 35h operates in the same manner as the reading circuit 15h shown in FIG. 3. A subsequent data processing stage 35i operates in the same manner as the subsequent data processing stage 15i shown in FIG. 3.

As shown in FIG. 11, the event data acquiring unit 35 includes a delay circuit 35s disposed at a preceding stage of the reading circuit 35h. The control signal 35q transmitted from the feedback circuit 35g is output to the reading circuit 35h via the delay circuit 35s. Further, the counter 35f transfers the count rate information 35p to the feedback circuit 35g.

Next, a third embodiment will be explained. The PET apparatus 100 according to the third embodiment regulates the amount of the event data read from the buffer by judging whether it is currently a high count rate period based on buffer free-space information indicating the amount of free space in the buffer and regulating the amount of the event data to be written into the buffer.

Figure 12:
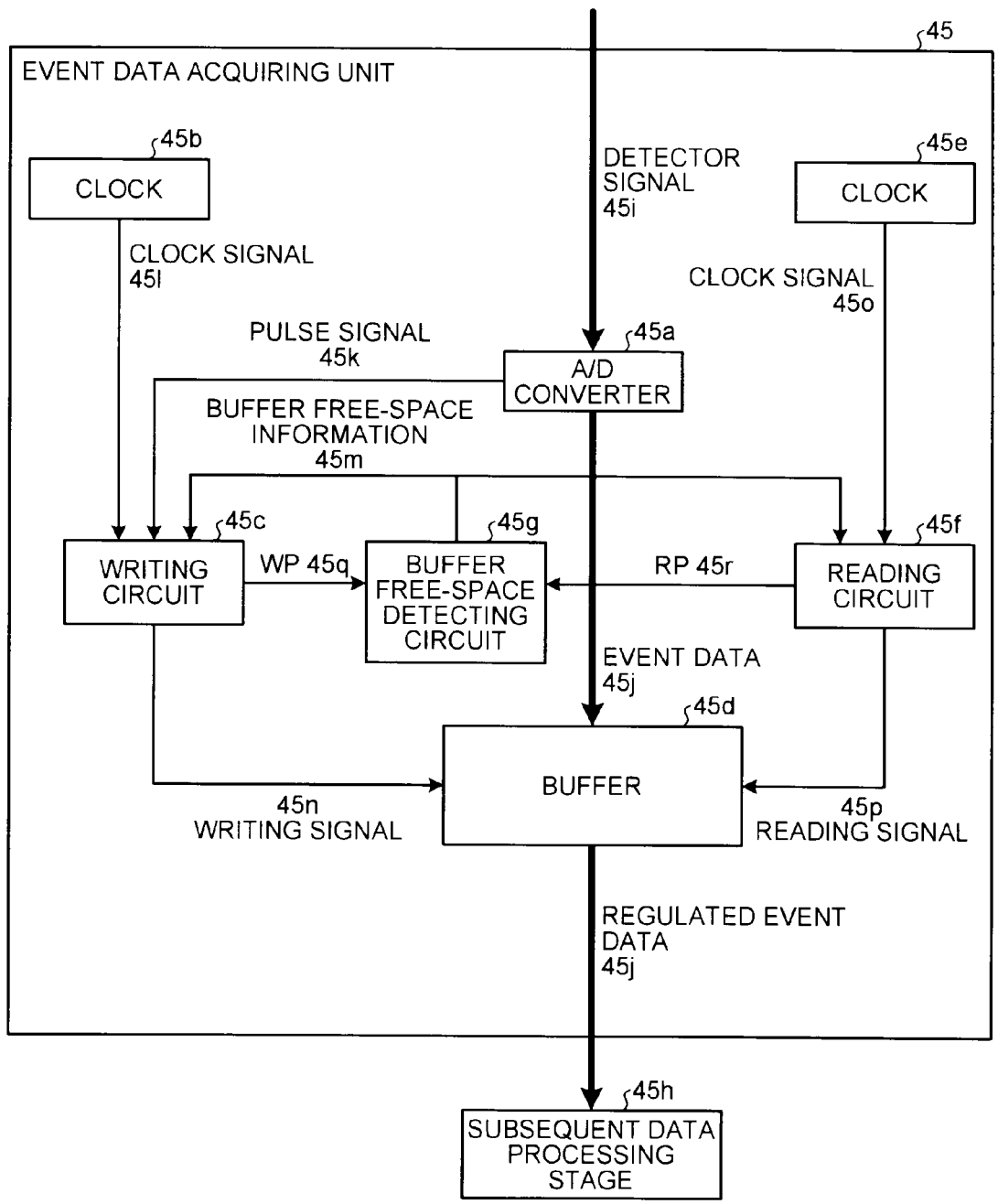
FIG. 12 is a block diagram of an event data acquiring unit according to a third embodiment.

FIG. 12 is a block diagram of an event data acquiring unit 45 according to the third embodiment. As shown in FIG. 12, the event data acquiring unit 45 includes an A/D converter 45a, a clock 45b, a writing circuit 45c, a buffer 45d, another clock 45e, a reading circuit 45f, and a buffer free-space detecting circuit 45g.

The third embodiment will be explained while a focus is placed on differences from the first and the second embodiments. As shown in FIG. 12, the event data acquiring unit 45 includes the buffer free-space detecting circuit 45g. The buffer free-space detecting circuit 45g monitors the amount of free space in the buffer 45d. More specifically, the buffer free-space detecting circuit 45g receives an input of a Write Pointer (WP) 45q from the writing circuit 45c, and also, receives an input of a Read Pointer (RP) 45r from the reading circuit 45f. Further, the buffer free-space detecting circuit 45g generates buffer free-space information 45m based on the WP 45q and the RP 45r and outputs the generated buffer free-space information 45m to the writing circuit 45c and the reading circuit 45f.

The reading circuit 45f receives an input of a clock signal 45o and generates a reading signal 45p according to the clock signal 45o. Also, when recognizing that the buffer 45d does not have event data 45j stored therein based on the buffer free-space information 45m, the reading circuit 45f performs no reading operation.

Figure 13:
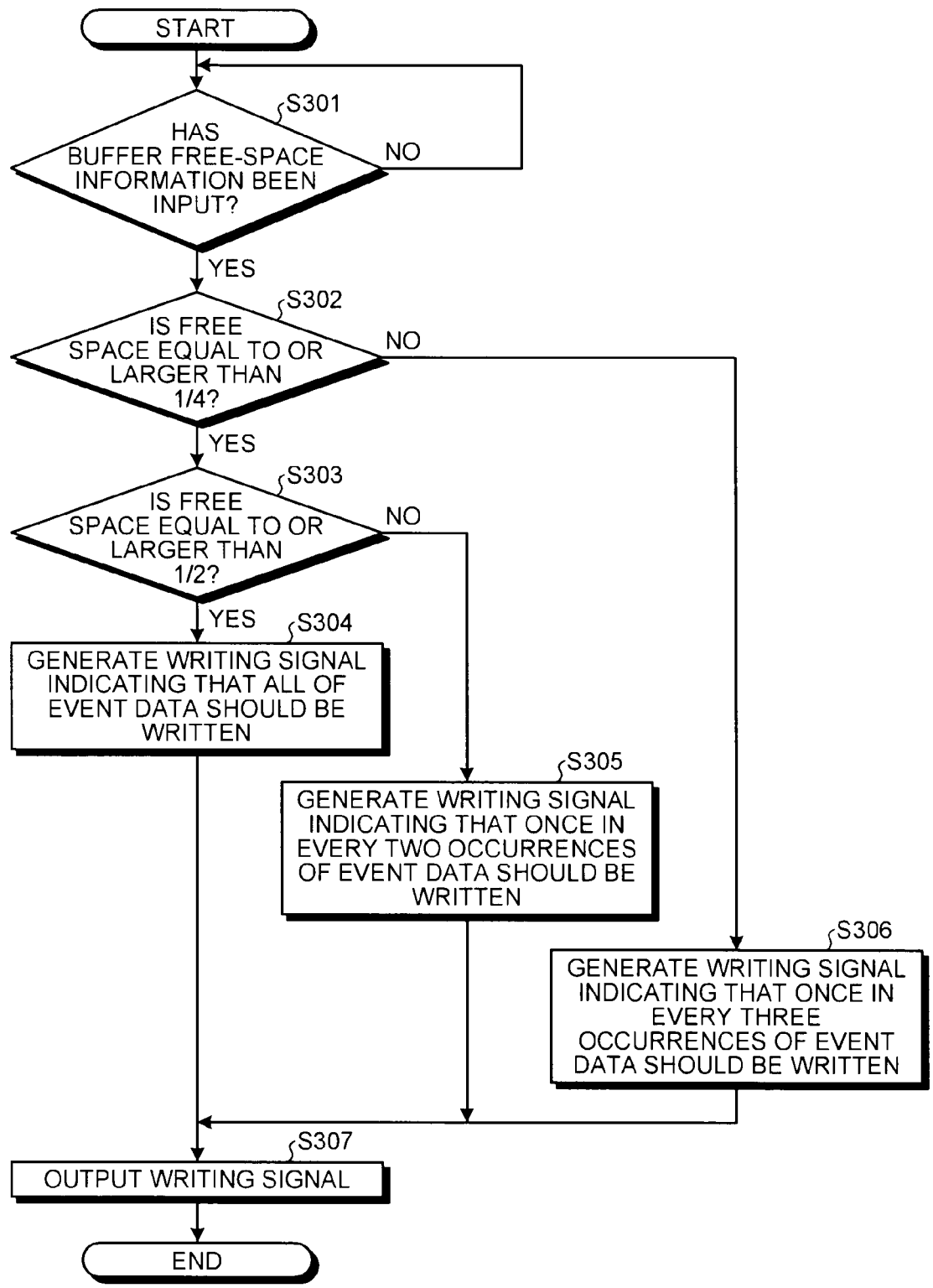
FIG. 13 is a flowchart of a processing procedure performed by a writing circuit according to the third embodiment.

In this situation, according to the third embodiment, the writing circuit 45c regulates the amount of the event data to be written into the buffer 45d. More specifically, the writing circuit 45c recognizes that there is event data 45j to be written into the buffer 45d by receiving an input of a pulse signal 45k. Also, the writing circuit 45c receives an input of the buffer free-space information 45m and judges whether it is currently a high count rate period based on the buffer free-space information 45m. Further, depending on whether it is currently a high count rate period, the writing circuit 45c controls the writing of the event data 45j. FIG. 13 is a flowchart of a processing procedure performed by the writing circuit 45c according to the third embodiment.

As shown in FIG. 13, when having received an input of the buffer free-space information 45m (step S301: Yes), the writing circuit 45c judges whether the amount of free space in the buffer indicated by the buffer free-space information 45m is equal to or larger than one-fourth (step S302). If the amount of free space is equal to or larger than one-fourth (step S302: Yes), the writing circuit 45c further judges whether the amount of free space is equal to or larger than one-half. If the amount of free space is equal to or larger than one-half (step S303: Yes), the writing circuit 45c generates a writing signal 45n indicating that all of the event data 45j recognized based on the pulse signal 45k should be written into the buffer 45d (step S304).

In contrast, if the amount of free space is equal to or larger than one-fourth (step S302: Yes), but is not equal to or larger than one-half (step S303: No), the writing circuit 45c generates a writing signal 45n indicating that, of the event data 45j recognized based on the pulse signal 45k, once in every two occurrences of event data 45j should be written (step S305).

In another situation, if the amount of free space is not equal to or larger than one-fourth (step S302: No), the writing circuit 45c generates a writing signal 45n indicating that, of the event data 45j recognized based on the pulse signal 45k, once in every three occurrences of event data 45j should be written (step S306).

Further, the writing circuit 45c outputs the writing signal 45n generated at step S304, step S305, or step S306 to the buffer 45d (step S307). Subsequently, the buffer 45d writes or discards the event data 45j of which the input was received from the A/D converter 45a, according to the writing signal 45n.

As explained above, the PET apparatus 100 according to the third embodiment regulates the amount of the event data read from the buffer during the high count rate period. More specifically, the PET apparatus 100 judges whether it is currently a high count rate period based on the buffer free-space information, and if the PET apparatus 100 determines that it is currently a high count rate period, the PET apparatus 100 regulates the amount of the data read from the buffer by regulating the amount of the data written into the buffer.

In the third embodiment, the method was explained by which the amount of the event data to be written into the buffer is varied according to the amount of free space in the buffer. However, the exemplary embodiments are not limited to this example. For instance, another method is acceptable by which a writing signal indicating that event data should be written at fixed intervals is generated, depending on whether there is free space in the buffer.

Next, a fourth embodiment will be explained. While using the method according to the third embodiment as a base, the PET apparatus 100 according to the fourth embodiment executes control so that the regulations on the amounts of the event data for the different blocks are synchronized among all the blocks.

Figure 14:
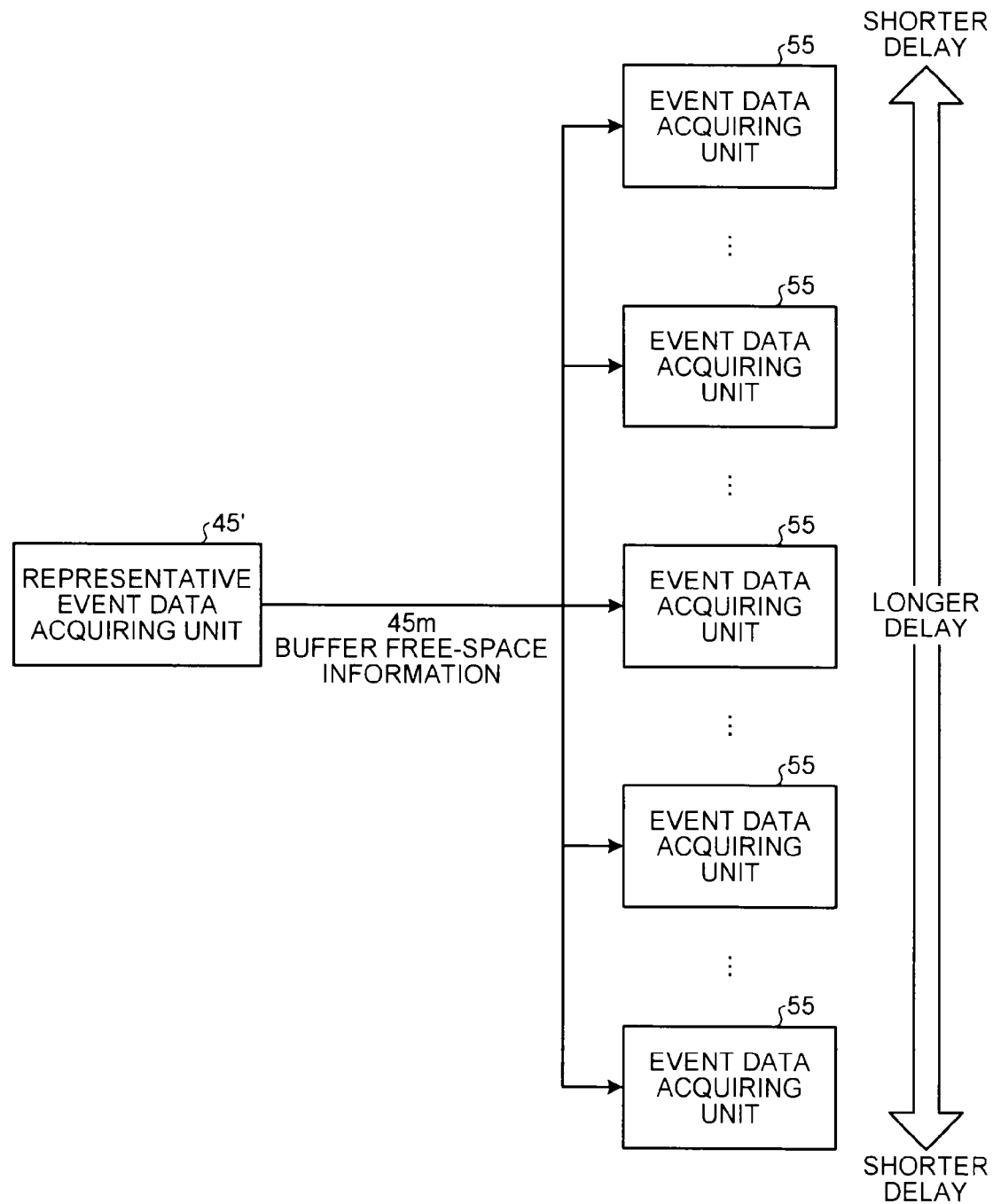
FIG. 14 is a drawing for explaining synchronization among the blocks according to a fourth embodiment.

In the fourth embodiment, the plurality of detector modules 14 are divided into a plurality of blocks. For example, one detector module 14 forms one block. FIG. 14 is a drawing for explaining the synchronization among the blocks according to the fourth embodiment. As explained with reference to FIG. 6, in the fourth embodiment also, of the detector modules 14 arranged in the ring formation so as to surround the examined subject P, a detector module 14 positioned on the left side, for example, is designated as a representative detector module 14. The representative detector module 14 includes a representative event data acquiring unit 45'. Each of the other detector modules 14 includes an event data acquiring unit 55. Further, the representative event data acquiring unit 45' transmits the buffer free-space information 45m to the other event data acquiring units 55. The other event data acquiring units 55 regulate the amount of the event data written into the buffer according to the buffer free-space information 45*m* transmitted from the representative event data acquiring unit 45'.

In this situation, to realize the synchronization among the blocks, it is desirable to configure the buffer free-space information 45*m* so as to arrive at all the detector modules 14 at the same time. For this reason, as shown in FIG. 14, delay circuits having mutually-different delay periods according to distances from the representative event data acquiring unit 45' are inserted. In other words, a delay circuit having the longest delay period is inserted for the representative event data acquiring unit 45'. For the other event data acquiring units 55, the delay circuits are inserted in such a manner that the longer the distance from the representative event data acquiring unit 45' is, the shorter is the delay period. The delay periods may be set to values that are calculated in a calibration process performed in advance.

Figure 15:
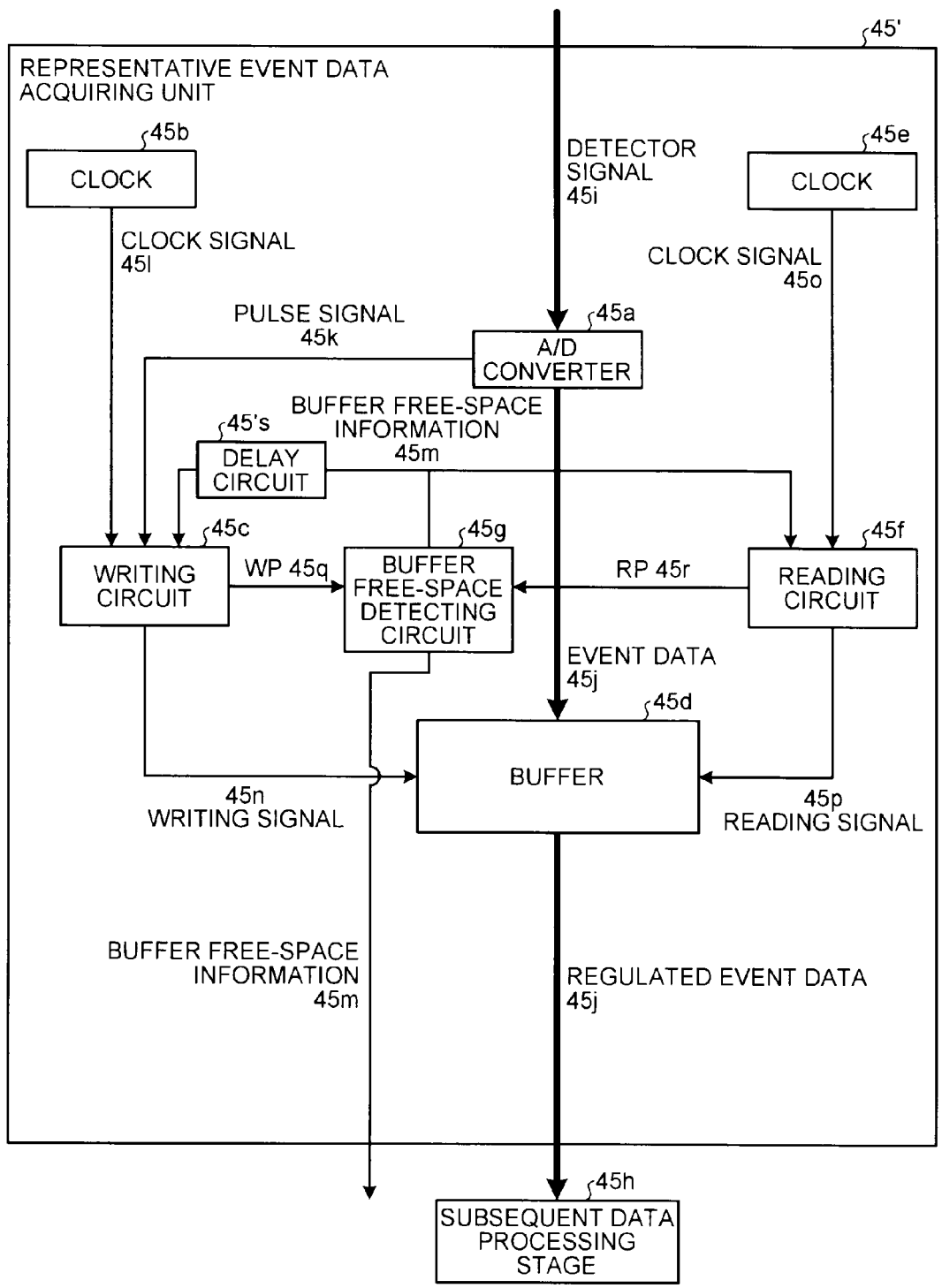
FIG. 15 is a block diagram of a representative event data acquiring unit according to the fourth embodiment.

FIG. 15 is a block diagram of the representative event data acquiring unit 45' according to the fourth embodiment. In FIG. 15, some of the functional units that operate in the same manner as those in the event data acquiring unit 45 explained with reference to FIG. 12 will be referred to by using the same reference characters as in FIG. 12.

As shown in FIG. 15, the representative event data acquiring unit 45' includes a delay circuit 45's disposed between the buffer free-space detecting circuit 45*g* and the writing circuit 45*c*. In other words, the buffer free-space detecting circuit 45*c*. In other words, the buffer free-space detecting circuit 45*g* outputs the generated buffer free-space information 45*m* to the writing circuit 45*c* via the delay circuit 45's, instead of outputting the generated buffer free-space information 45*m* directly to the writing circuit 45*c*. Further, the buffer free-space detecting circuit 45*g* transfers the buffer free-space information 45*m* to the other event data acquiring units 55.

Figure 16:
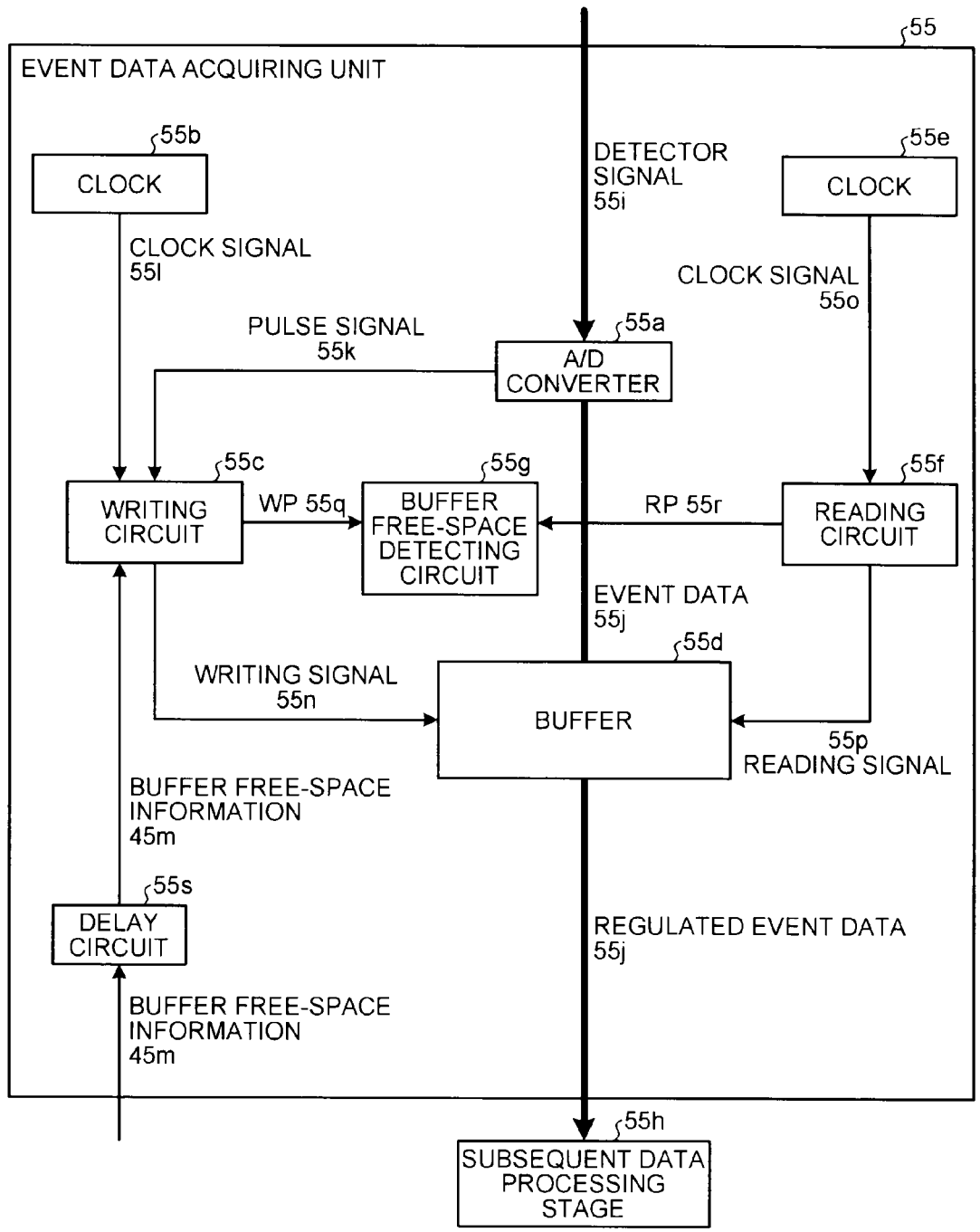
FIG. 16 is a block diagram of an event data acquiring unit according to the fourth embodiment.

FIG. 16 is a block diagram of the event data acquiring unit 55 according to the fourth embodiment. As shown in FIG. 16, the event data acquiring unit 55 includes a delay circuit 55*s* disposed at a preceding stage of a writing circuit 55*c*. The buffer free-space information 45*m* transmitted from the representative event data acquiring unit 45' is output to the writing circuit 55*c* via the delay circuit 55*s*.

In this situation, when the buffer free-space information 45*m* is, for example, 4-bit information, it is considered to be difficult to achieve sufficient synchronization among the blocks, even if the delay circuit 55*s* is inserted. In that situation, the timing with which the writing circuit 55*c* checks for the buffer free-space information 45*m* is arranged to be at predetermined time intervals. For example, the writing circuit 55*c* is configured so as to check for the buffer free-space information 45*m* once every 10 clocks of a clock signal 55*l*. By configuring the checking timing so as to be at the predetermined time intervals in this manner, it is possible to synchronize the checking timing even if, for example, the pieces of 4-bit information arrive at the blocks out of synchronization, and it is possible to synchronize the control executed over the writing processes performed by the writing circuit 55*c*. In another example, another method is also acceptable by which the quantity of buses used for transmitting and receiving data among the blocks is increased so that, for example, the pieces of 4-bit information arrive all at once.

As explained above, the PET apparatus 100 according to the fourth embodiment executes control so that the regulations on the amounts of the event data for the different blocks are synchronized among all the blocks. Thus, it is possible to appropriately regulate the amount of the event data.

The exemplary embodiments are not limited to the first to the fourth embodiments described above. For example, in the first to the fourth embodiments, the regulations on the amounts of the event data read from the buffer are explained as a process performed in the event data acquiring units included in the detector modules; however, the exemplary embodiments are not limited to this example. The problem related to a high count rate period may similarly occur, for instance, on the console device 16 side shown in FIG. 1. To cope with situation, it is possible to similarly apply, for example, the control using the ring buffer as explained in the first embodiment and/or the control during the writing process as explained in the third embodiment.

Further, in the second and the fourth embodiments, the detector module positioned on the left side is designated as the representative detector module. The reason is that, of the plurality of detector modules, the detector modules positioned on both sides have a high possibility of having a high count rate. Accordingly, the detector module positioned on the right side may be designated as the representative detector module. Alternatively, any other detector module may be designated as the representative detector module.

By using the PET apparatus according to at least one of the exemplary embodiments described above, it is possible to regulate the amount of the event data read from the buffer during a high count rate period of the events at which the annihilation radiation is detected. Thus, it is possible to appropriately regulate the amount of the event data during the high count rate period. As a result, it is possible to guarantee sufficient image quality even during the high count rate period.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A positron emission computed tomography apparatus, comprising:
   a detector configured to detect annihilation radiation;
   a buffer configured to store therein event data generated based on an output signal from the detector; and
   an event data acquiring circuit configured to regulate an amount of event data read from the buffer and output to a subsequent data processing stage, wherein the amount of event data read from the buffer is less than a total amount of event data in the buffer, when a count rate of the annihilation radiation exceeds a predetermined threshold value.

2. The positron emission computed tomography apparatus according to claim 1, wherein the event data acquiring circuit regulates the amount of the event data read from the buffer and output to the subsequent data processing stage in such a manner that pieces of event data that can form a pair representing a pair of annihilation radiation rays that are counted coincidentally are discarded together.

3. The positron emission computed tomography apparatus according to claim 2, wherein
   the detector is divided into a plurality of blocks,
   the buffer and the even data acquiring circuit are provided for each of the blocks, and
   the event data acquiring circuit executes control so that regulations on the amounts of the event data for the blocks are synchronized among all the blocks.

4. The positron emission computed tomography apparatus according to claim 3, wherein
the buffer includes a plurality of buffer areas,
the positron emission computed tomography apparatus further comprises: a generating unit configured to generate count rate information indicating the count rate of the output signal, and
the event data acquiring circuit judges whether it is currently a high count rate period based on the count rate information and the predetermined threshold value and, when the event data acquiring circuit determines that it is currently the high count rate period, the event data acquiring circuit reads the event data from a part of the plurality of buffer areas included in the buffer.

5. The positron emission computed tomography apparatus according to claim 4, wherein the event data acquiring circuit varies a quantity of buffer areas serving as the part of the plurality of buffer areas, according to the count rate.

6. The positron emission computed tomography apparatus according to claim 3, further comprising: a free-space information generating unit configured to generate buffer free-space information indicating an amount of free space in the buffer, wherein
the event data acquiring circuit judges whether it is currently a high count rate period based on the buffer free-space information and, when the event data acquiring circuit determines that it is currently the high count rate period, the event data acquiring circuit regulates the amount of the event data read from the buffer and output to the subsequent data processing stage by regulating an amount of event data to be written into the buffer.

7. The positron emission computed tomography apparatus according to claim 6, wherein the event data acquiring circuit varies the amount of the event data to be written into the buffer, according to the amount of the free space in the buffer.

8. The positron emission computed tomography apparatus according to claim 2, wherein
the buffer includes a plurality of buffer areas,
the positron emission computed tomography apparatus further comprises: a generating unit configured to generate count rate information indicating the count rate of the output signal, and
the event data acquiring circuit judges whether it is currently a high count rate period based on the count rate information and the predetermined threshold value and, when the event data acquiring circuit determines that it is currently the high count rate period, the event data acquiring circuit reads the event data from a part of the plurality of buffer areas included in the buffer.

9. The positron emission computed tomography apparatus according to claim 8, wherein the event data acquiring circuit varies a quantity of buffer areas serving as the part of the plurality of buffer areas, according to the count rate.

10. The positron emission computed tomography apparatus according to claim 2, further comprising: a free-space information generating unit configured to generate buffer free-space information indicating an amount of free space in the buffer, wherein
the event data acquiring circuit judges whether it is currently a high count rate period based on the buffer free-space information and, when the event data acquiring circuit determines that it is currently the high count rate period, the event data acquiring circuit regulates the amount of the event data read from the buffer and output to the subsequent data processing stage by regulating an amount of event data to be written into the buffer.

11. The positron emission computed tomography apparatus according to claim 10, wherein the event data acquiring circuit varies the amount of the event data to be written into the buffer, according to the amount of the free space in the buffer.

12. The positron emission computed tomography apparatus according to claim 1, wherein
the buffer includes a plurality of buffer areas,
the positron emission computed tomography apparatus further comprises: a generating unit configured to generate count rate information indicating the count rate of the output signal, and
the event data acquiring circuit judges whether it is currently a high count rate period based on the count rate information and the predetermined threshold value and, when the even data acquiring circuit determines that it is currently the high count rate period, the event data acquiring circuit reads the event data from a part of the plurality of buffer areas included in the buffer.

13. The positron emission computed tomography apparatus according to claim 12, wherein the event data acquiring circuit varies a quantity of buffer areas serving as the part of the plurality of buffer areas, according to the count rate.

14. The positron emission computed tomography apparatus according to claim 1, further comprising: a free-space information generating unit configured to generate buffer free-space information indicating an amount of free space in the buffer, wherein
the event data acquiring circuit judges whether it is currently a high count rate period based on the buffer free-space information and, when the event data acquiring circuit determines that it is currently the high count rate period, the event data acquiring circuit regulates the amount of the event data read from the buffer and output to the subsequent data processing stage by regulating an amount of event data to be written into the buffer.

15. The positron emission computed tomography apparatus according to claim 14, wherein the event data acquiring circuit varies the amount of the event data to be written into the buffer, according to the amount of the free space in the buffer.

* * * * *